(12) United States Patent
Timken et al.

(10) Patent No.: US 11,306,253 B2
(45) Date of Patent: *Apr. 19, 2022

(54) CIRCULAR ECONOMY FOR PLASTIC WASTE TO POLYETHYLENE VIA REFINERY FCC OR FCC/ALKYLATION UNITS

(71) Applicant: Chevron U.S.A. Inc., San Ramon, CA (US)

(72) Inventors: Hye-Kyung Timken, Albany, CA (US); Cameron McCord, San Ramon, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/131,910

(22) Filed: Dec. 23, 2020

(65) Prior Publication Data

US 2021/0301209 A1  Sep. 30, 2021

Related U.S. Application Data (60) Provisional application No. 63/002,020, filed on Mar. 30, 2020.

(51) Int. Cl.
  *C10B 53/07* (2006.01)
  *C10G 51/04* (2006.01)
  (Continued)

(52) U.S. Cl.
  CPC .............. *C10B 53/07* (2013.01); *C10G 9/36* (2013.01); *C10G 31/06* (2013.01); *C10G 35/02* (2013.01);
  (Continued)

(58) Field of Classification Search
  None
  See application file for complete search history.

(56) References Cited

U.S. PATENT DOCUMENTS 3,845,157 A  10/1974  Woo et al.
4,642,401 A   2/1987  Coenen et al.
(Continued)

FOREIGN PATENT DOCUMENTS

EP     0620264 A2   10/1994

OTHER PUBLICATIONS

International Search Report from PCT/US2020/66822 dated May 21, 2021.

(Continued)

*Primary Examiner* — Philip Y Louie
(74) *Attorney, Agent, or Firm* — E. Joseph Gess; Melissa M. Hayworth; Terrence M. Flaherty (57) ABSTRACT

Provided in one embodiment is a continuous process for converting waste plastic into recycle for polyethylene polymerization. The process comprises selecting waste plastics containing polyethylene and/or polypropylene, and passing the waste plastics through a pyrolysis reactor to thermally crack at least a portion of the polyolefin waste and produce a pyrolyzed effluent. The pyrolyzed effluent is separated into offgas, a pyrolysis oil and optionally wax comprising a naphtha/diesel and heavy fraction, and char. The pyrolysis oil is passed to a refinery FCC unit from which a liquid petroleum gas $C_3$ olefin/paraffin mixture fraction is recovered, as well as a $C_4$ olefin/paraffin mixture fraction. The liquid petroleum gas $C_3$ olefin/paraffin mixture fraction is passed to a steam cracker for ethylene production. The $C_4$ olefin/paraffin mixture fraction is passed to a refinery alkylation unit, from which a n-butane and naphtha feed for a stream cracker to produce ethylene is recovered.

22 Claims, 4 Drawing Sheets

Establishment of Circular Economy for Recycle of PE via Pyrolysis of PE/PP Waste Plastics Through Oil Refinery FCC Operation (51) Int. Cl.
*C10G 57/02* (2006.01)
*C10G 31/06* (2006.01)
*C10G 35/02* (2006.01)
*C10G 51/02* (2006.01)
*C10G 9/36* (2006.01)

(52) U.S. Cl.
CPC ........... *C10G 51/023* (2013.01); *C10G 57/02* (2013.01); *C10G 2300/1003* (2013.01); *C10G 2300/1044* (2013.01); *C10G 2400/06* (2013.01); *C10G 2400/20* (2013.01); *C10G 2400/28* (2013.01)

(56) References Cited

U.S. PATENT DOCUMENTS

| | | | |
|---|---|---|---|
| 5,849,964 | A | 12/1998 | Holighaus et al. |
| 5,981,818 | A * | 11/1999 | Purvis ..................... C07C 4/02 526/75 |
| 6,143,940 | A | 11/2000 | Miller et al. |
| 6,150,577 | A | 11/2000 | Miller et al. |
| 6,288,296 | B1 | 9/2001 | Miller et al. |
| 6,774,272 | B2 | 8/2004 | Miller |
| 6,822,126 | B2 | 11/2004 | Miller |
| 7,834,226 | B2 | 11/2010 | Miller |
| 8,088,961 | B2 | 1/2012 | Miller |
| 8,404,912 | B1 | 3/2013 | Miller |
| 8,480,880 | B2 | 7/2013 | Miller |
| 8,696,994 | B2 | 4/2014 | Miller |
| 2006/0089518 | A1 | 4/2006 | Bouvart et al. |
| 2007/0238912 | A1 * | 10/2007 | Smith ..................... C07C 2/62 585/716 |
| 2016/0168481 | A1 * | 6/2016 | Ray ..................... C10G 33/04 585/350 |
| 2016/0264885 | A1 | 9/2016 | Narayanaswamy et al. |
| 2016/0362609 | A1 | 12/2016 | Ward et al. |
| 2019/0161683 | A1 | 5/2019 | Narayanaswamy et al. |
| 2019/0367428 | A1 | 12/2019 | Ramamurthy et al. |
| 2021/0130699 | A1 * | 5/2021 | Bitting ..................... C10G 1/10 |
| 2021/0189248 | A1 | 6/2021 | Timken |
| 2021/0189250 | A1 | 6/2021 | Timken |
| 2021/0189251 | A1 | 6/2021 | Timken |
| 2021/0189252 | A1 | 6/2021 | Timken |
| 2021/0189253 | A1 | 6/2021 | Timken |
| 2021/0189254 | A1 | 6/2021 | Timken |
| 2021/0189269 | A1 | 6/2021 | Timken |

OTHER PUBLICATIONS

Written Opinion from PCT/US2020/66822 dated May 21, 2021.
Filtration product information "Refineries: Application Focus—HF Alkylation", Pall Corporation, (2018) https://www.pall.co.uk/content/dam/pall/oil-gas/literature-library/non-gated/pdf/refinery-hf-alkylation.pdf.
Seaman, Greg, "Plastics by the Numbers", eartheasy, (2012) https://learn.eartheasy.com/articles/plastics-by-the-numbers/.

* cited by examiner

Figure 2

Establishment of Circular Economy for Recycle of PE via Pyrolysis of PE/PP Waste Plastics Through Oil Refinery FCC Operation Figure 3
Establishment of Circular Economy for Recycle of PE via Pyrolysis of PE/PP Waste Plastics Through Oil Refinery FCC/ Alky Operation Figure 4
Plastic Type Classification for Waste Plastics Recycling

CIRCULAR ECONOMY FOR PLASTIC WASTE TO POLYETHYLENE VIA REFINERY FCC OR FCC/ALKYLATION UNITS

CROSS REFERENCE TO RELATED APPLICATIONS

The present application claims priority to U.S. Provisional Application No. 63/002,020 filed Mar. 30, 2020, the complete disclosure of which is incorporated herein by reference in its entirety.

BACKGROUND

The world has seen extremely rapid growth of plastics production. According to PlasticsEurope Market Research Group, the world plastics production was 335 million tons in 2016, 348 million tons in 2017 and 359 million tons in 2018. According to McKinsey & Company, the global plastics-waste volume was estimated about 260 million tons per year in 2016, and projected to be 460 million tons per year by 2030 if the current trajectory continues.

Single use plastic waste has become an increasingly important environmental issue. At the moment, there appear to be few options for recycling polyethylene and polypropylene waste plastics to value-added chemical and fuel products. Currently, only a small amount of polyethylene and polypropylene is recycled via chemical recycling, where recycled and cleaned polymer pellets are pyrolyzed in a pyrolysis unit to make fuels (naphtha, diesel), stream cracker feed or slack wax.

Processes are known which convert waste plastic into hydrocarbon lubricants. For example, U.S. Pat. No. 3,845,157 discloses cracking of waste or virgin polyolefins to form gaseous products such as ethylene/olefin copolymers which are further processed to produce synthetic hydrocarbon lubricants. U.S. Pat. No. 4,642,401 discloses the production of liquid hydrocarbons by heating pulverized polyolefin waste at temperatures of 150-500° C. and pressures of 20-300 bars. U.S. Pat. No. 5,849,964 discloses a process in which waste plastic materials are depolymerized into a volatile phase and a liquid phase. The volatile phase is separated into a gaseous phase and a condensate. The liquid phase, the condensate and the gaseous phase are refined into liquid fuel components using standard refining techniques. U.S. Pat. No. 6,143,940 discloses a procedure for converting waste plastics into heavy wax compositions. U.S. Pat. No. 6,150,577 discloses a process of converting waste plastics into lubricating oils. EP0620264 discloses a process for producing lubricating oils from waste or virgin polyolefins by thermally cracking the waste in a fluidized bed to form a waxy product, optionally using a hydrotreatment, then catalytically isomerizing and fractionating to recover a lubricating oil.

Other documents which relate to processes for converting waste plastic into lubricating oils include U.S. Pat. Nos. 6,288,296; 6,774,272; 6,822,126; 7,834,226; 8,088,961; 8,404,912; and 8,696,994; and U.S. Patent Publication Nos. 2019/0161683; 2016/0362609; and 2016/0264885. The foregoing patent documents are incorporated herein by reference in their entirety.

The current method of chemical recycling via pyrolysis cannot make a big impact for the plastics industry. The current pyrolysis operation produces poor quality fuel components (naphtha and diesel range products), but the quantity is small enough that these products can be blended into fuel supplies. However, this simple blending cannot continue if very large volumes of waste polyethylene and polypropylene are to be recycled to address environmental issues. The products as produced from a pyrolysis unit are of too poor quality to be blended in large amounts (for example 5-20 vol. % blending) in transportation fuels.

In order to achieve recycling of single use plastics in an industrially significant quantity to reduce its environmental impact, more robust processes are needed. The improved processes should establish "circular economy" for the waste polyethylene and polypropylene plastics where the spent waste plastics are recycled effectively back as starting materials for the polymers and high value byproducts.

SUMMARY

Provided is a continuous process for converting waste plastic into recycle for polyethylene polymerization. The process comprises selecting waste plastics containing polyethylene and/or polypropylene. These waste plastics are then passed through a pyrolysis reactor to thermally crack at least a portion of the polyolefin waste and produce a pyrolyzed effluent. The pyrolyzed effluent is separated into offgas, a pyrolysis oil and optionally pyrolysis wax comprising a naphtha/diesel and heavy fraction, and char.

The incorporation of the process with an oil refinery is an important aspect of the present process, and allows the creation of a circular economy with a single use waste plastic such as polyethylene. Thus, the pyrolysis oil, the entire liquid fraction from the pyrolysis unit, is passed to a refinery FCC unit from which can be recovered liquid petroleum olefin streams. These liquid petroleum olefin streams can be passed directly to a steam cracker for ethylene production, or to a refinery alkylation unit from which is recovered an alkylate gasoline and $nC_4$ fraction. This fraction $nC_4$ is then passed to a steam cracker for ethylene production.

The refinery will generally have its own hydrocarbon feed flowing through the refinery units. The flow volume of pyrolysis oil and wax generated from the pyrolysis of waste plastic to the refinery units can comprise any practical or accommodating volume % of the total flow to the refinery units. Generally, the flow of the pyrolysis oil and wax generated from the waste plastic pyrolysis, for practical reasons, can be up to about 50 vol. % of the total flow, i.e., the refinery flow and the pyrolysis flow. In one embodiment, the flow of the pyrolysis oil and wax is an amount up to about 20 vol. % of the total flow.

In another embodiment, a continuous process for converting waste plastic comprising polyethylene into recycle for polyethylene polymerization is provided. The process comprises selecting waste plastics containing polyethylene and polypropylene and then passing the waste plastics through a pyrolysis reactor to thermally crack at least a portion of the polyolefin waste and produce a pyrolyzed effluent. The pyrolyzed effluent is separated into offgas, a pyrolysis oil comprising a naphtha/diesel fraction and a heavy fraction, and char. The pyrolysis oil, the entire liquid and wax fraction from the pyrolysis unit, is passed to a refinery FCC unit. The FCC unit will eliminate any contaminants in the pyrolysis oil and convert it into FCC hydrocarbon product. The FCC product is sent to the FCC unit separation section to produce offgas, $C_3$, $C_4$, FCC gasoline and heavy fractions. From the separation section, a clean $C_3$ liquid petroleum gas (LPG) fraction containing propane and propylene is collected. The $C_3$ stream is a good feed for a steam cracker. The $C_3$ stream is fed to a steam cracker distillation section to separate into propane and propylene. Then, propane is fed to the steam cracker reactor to be converted to pure ethylene.

The $C_4$ LPG fraction recovered contains butanes and butenes and is sent to an alkylation unit to produce n-butane and alkylate. These streams are rich in linear paraffins and a very good naphtha feed for a stream cracker to generate ethylene.

The FCC gasoline is sent to a gasoline blending pool. A portion of the alkylate gasoline recovered from the alkylation unit can be combined/blended with the FCC gasoline fraction. The heavy portion of the hydrocarbon from the FCC unit distillation is sent to appropriate refinery units for upgrading into clean gasoline and diesel.

Among other factors, it has been found that by adding refinery operations one can upgrade the waste pyrolysis oil and wax to higher value products such as gasoline and diesel. Also, by adding refinery operations it has been found that clean naphtha ($C_5$-$C_8$) or $C_4$ or $C_3$ can be efficiently and effectively produced from the waste pyrolysis oil for ultimate polyethylene polymer production. Positive economics are realized for the overall process from recycled plastics to a polyethylene product with product quality identical to that of virgin polymer.

DETAILED DESCRIPTION

In the present process, provided is a method to recycle waste polyethylene and/or polypropylene back to virgin polyethylene to establish the circular economy by combining distinct industrial processes. A substantial portion of polyethylene and polypropylene polymers are used in single use plastics and get discarded after its use. The single use plastic waste has become an increasingly important environmental issue. At the moment, there appear to be few options for recycling polyethylene and polypropylene waste plastics to value-added chemicals and fuel products. Currently, only a small amount of polyethylene/polypropylene is recycled via chemical recycling, where recycled and cleaned polymer pellets are pyrolyzed in a pyrolysis unit to make fuels (naphtha, diesel), steam cracker feed or slack wax.

Ethylene is the most produced petrochemical building block. Ethylene is produced in hundreds of millions of tons per year via steam cracking. The steam crackers use either gaseous feedstocks (ethane, propane and/or butane) or liquid feed stocks (naphtha or gas oil). It is a noncatalytic cracking process operating at very high temperatures, up to 850° C.

Polyethylene is used widely in various consumer and industrial products. Polyethylene is the most common plastic, over 100 million tons of polyethylene resins are produced annually. Its primary use is in packaging (plastic bags, plastic films, geomembranes, containers including bottles, etc.). Polyethylene is produced in three main forms: high-density polyethylene (HDPE, ~0.940-0.965 $g/cm^{-3}$), linear low-density polyethylene (LLDPE, ~0.915-0.940 $g/cm^{-3}$) and low-density polyethylene (LDPE, (<0.930 $g/cm^{-3}$), with the same chemical formula $(C_2H_4)_n$ but different molecular structure. HDPE has a low degree of branching with short side chains while LDPE has a very high degree of branching with long side chains. LLDPE is a substantially linear polymer with significant numbers of short branches, commonly made by copolymerization of ethylene with short-chain alpha-olefins.

Low density polyethylene (LDPE) is produced via radical polymerization at 150-300° C. and very high pressure of 1,000-3,000 atm. The process uses a small amount of oxygen and/or organic peroxide initiator to produce polymer with about 4,000-40,000 carbon atoms per the average polymer molecule, and with many branches. High density polyethylene (HDPE) is manufactured at relatively low pressure (10-80 atm) and 80-150° C. temperature in the presence of a catalyst. Ziegler-Natta organometallic catalysts (titanium(III) chloride with an aluminum alkyl) and Phillips-type catalysts (chromium(IV) oxide on silica) are typically used, and the manufacturing is done via a slurry process using a loop reactor or via a gas phase process with a fluidized bed reactor. Hydrogen is mixed with ethylene to control the chain length of the polymer. Manufacturing conditions of linear low-density polyethylene (LLDPE) is similar to those of HDPE except copolymerization of ethylene with short-chain alpha-olefins (1-butene or 1-hexene).

Today, only a small portion of spent polyethylene products is collected for recycling efforts due to the inefficiencies discussed above.

Figure 1:
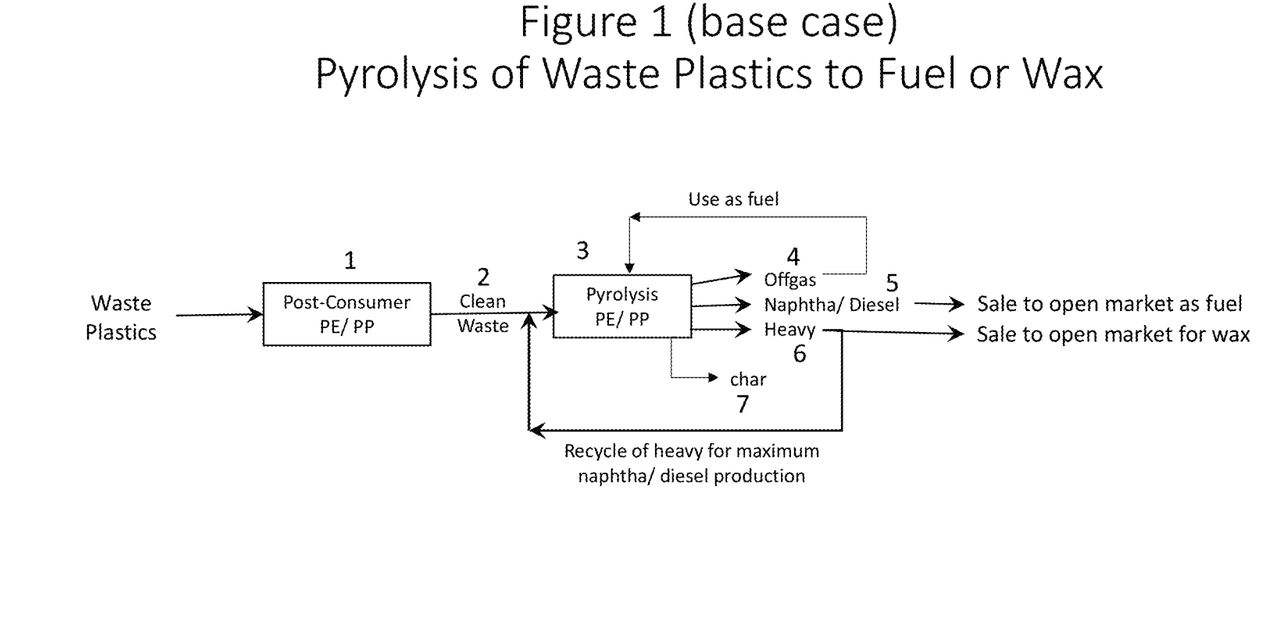
FIG. 1 depicts the current practice of pyrolyzing waste plastics to produce fuel or wax (base case).

FIG. 1 shows a diagram of pyrolysis of waste plastics fuel or wax that is generally operated in the industry today. As noted above, generally, polyethylene and polypropylene wastes are sorted together 1. The cleaned polyethylene/polypropylene waste 2 is converted in a pyrolysis unit 3 to offgas 4 and pyrolysis oil (liquid product). The offgas 4 from the pyrolysis unit is used as fuel to operate the pyrolysis unit. A distillation unit in the pyrolysis unit separates the pyrolysis oil to produce naphtha and diesel 5 products which are sold to fuel markets. The heavy pyrolysis oil fraction 6 is recycled back to the pyrolysis unit 3 to maximize the fuel yield. Char 7 is removed from the pyrolysis unit 3. The heavy fraction 6 is rich in long chain, linear hydrocarbons, and is very waxy (i.e., forms paraffinic wax upon cooling to ambient temperature). Wax can be separated from the heavy fraction 6 and sold to the wax markets.

The present process converts pyrolyzed polyethylene and/or polypropylene waste plastic in large quantities by integrating the waste polymer pyrolysis product streams into an oil refinery operation. The resulting processes produce the feedstocks for the polymers (naphtha or $C_3$-$C_4$ or $C_3$ only for ethylene cracker), high quality gasoline and diesel fuel.

Generally, the present process provides a circular economy for polyethylene plants. Polyethylene is produced via polymerization of pure ethylene. Clean ethylene can be made using a steam cracker. Either naphtha or a $C_3$ or $C_4$ stream can be fed to the steam cracker. The ethylene is then polymerized to create polyethylene.

By adding refinery operations to upgrade the waste pyrolysis oil to higher value products (gasoline and diesel) and to produce clean LPG and naphtha for steam cracker for ultimate polyethylene polymer production, one is able to create positive economics for the overall process from recycled plastics to polyethylene product with quality identical to that of the virgin polymer.

A pyrolysis unit produces poor quality products containing contaminants, such as calcium, magnesium, chlorides, nitrogen, sulfur, dienes, and heavy components, which products cannot be used in large quantity for blending in transportation fuels. It has been discovered that by having these products go through the refinery units, the contaminants can be captured in pre-treating units and their negative impacts diminished. The fuel components can be further upgraded with appropriate refinery units with chemical conversion processes, with the final transportation fuels produced by the integrated process being of higher quality and meeting the fuels quality requirements. The present process will upgrade the wax into valuable gasoline and diesel. The integrated process will generate much cleaner naphtha stream as steam cracker feedstock for ethylene generation and polyethylene production. These large on-spec productions allow "cyclical economy" for the recycle plastics feasible.

The carbon in and out of the refinery operations are "transparent," meaning that all the molecules from the waste plastic do not necessarily end up in the exact olefin product cycled back to the polyolefin plants, but are nevertheless assumed as "credit" as the net "green" carbon in and out of the refinery is positive. With these integrated processes, the amount of virgin feeds needed for polyethylene plants will be reduced substantially.

Figure 2:
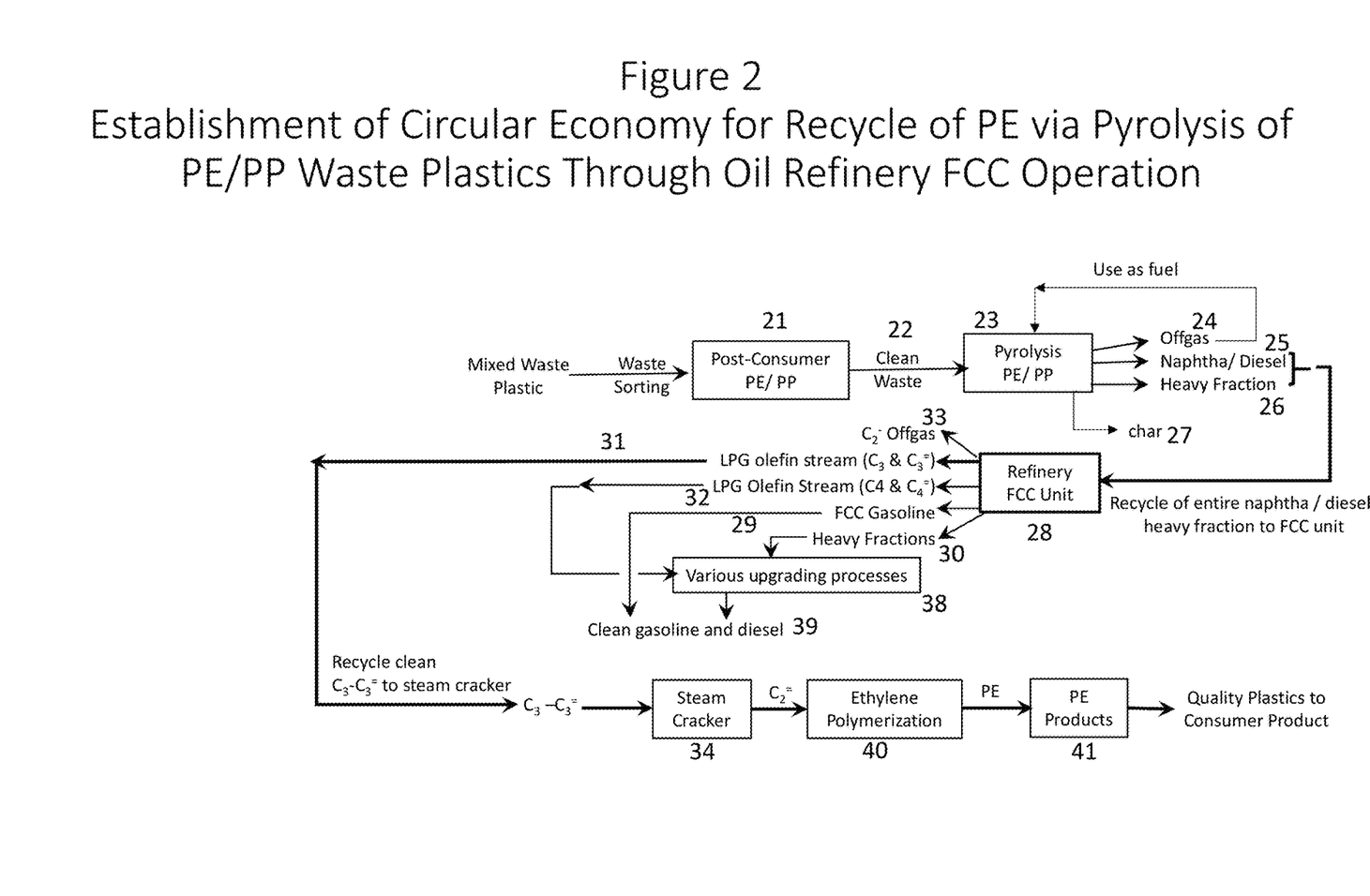
FIG. 2 depicts a present process for establishing a circular economy for waste plastics in accordance with the present processes.
Figure 3:
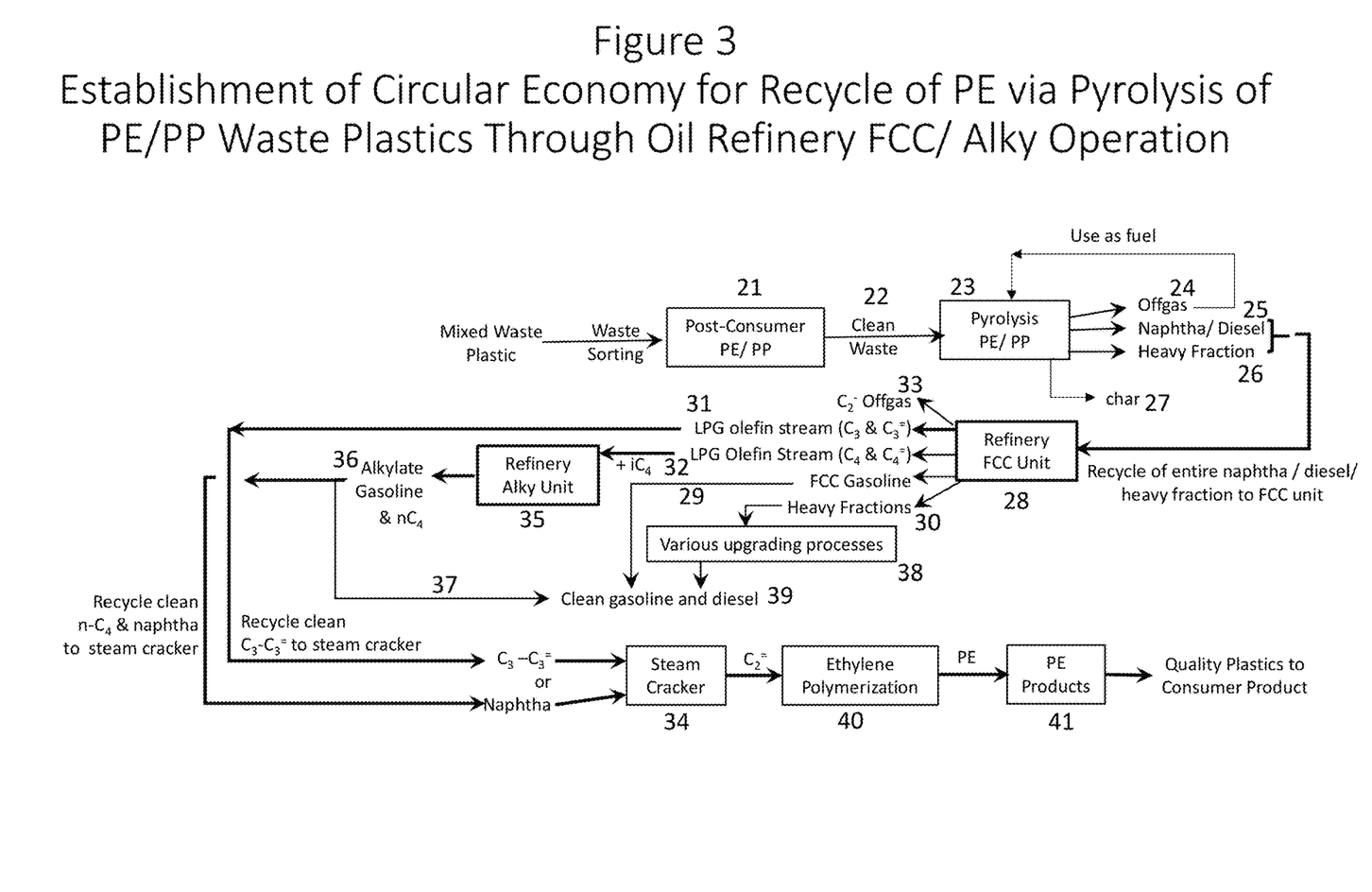
FIG. 3 depicts a present process for establishing a circular economy for waste plastics in accordance with the present processes, the process involving an alkylation unit.

FIG. 2 and FIG. 3 show present integrated processes, integrating refinery operations with recycle for effective polyethylene production. In FIG. 2 and FIG. 3, mixed waste plastics are sorted together 21. The cleaned waste plastic 22 is converted in a pyrolysis unit 23 to offgas 24 and a pyrolysis oil (liquid product) and optionally wax (solid product at ambient temperature). The offgas 24 from the pyrolysis unit can be used as fuel to operate the pyrolysis unit 23. The pyrolysis oil is separated, generally at an on-site distillation unit in the pyrolysis unit 23, into a naphtha/diesel fraction 25, and a heavy fraction 26. Char 27 is removed from the pyrolysis unit 23 after completion of the pyrolysis step.

The pyrolysis unit can be located near the waste plastics collection site, which site could be away from a refinery, near a refinery, or within a refinery. If the pyrolysis unit is located away from the refinery, then pyrolysis oil (naphtha/diesel and heavies) can be transferred to the refinery by truck, barge, rail car or pipeline. It is preferred, however, that the pyrolysis unit is within the waste plastics collection site or within the refinery.

Figure 4:
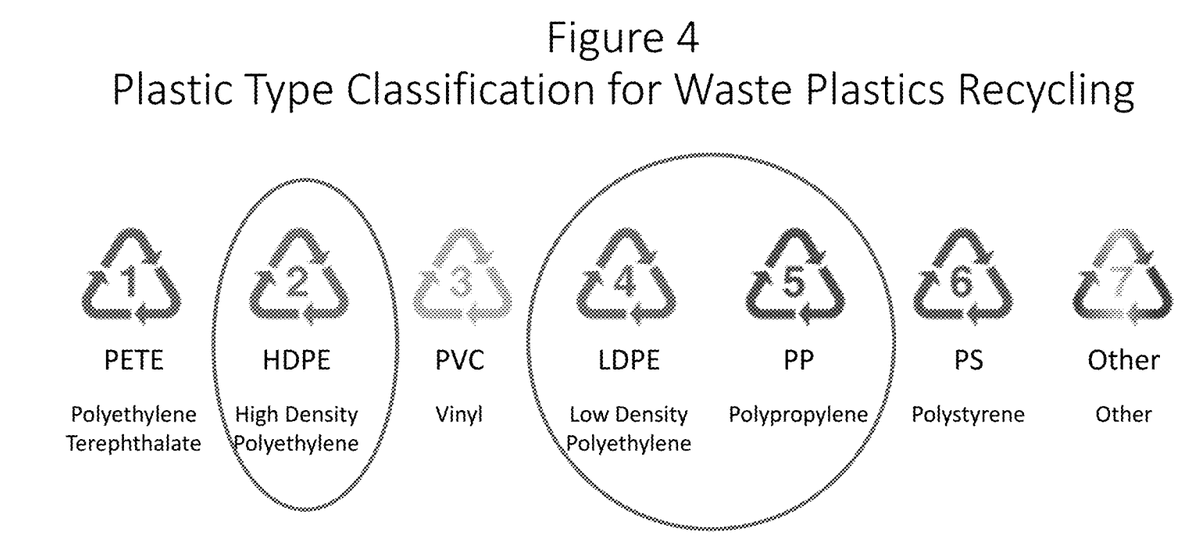
FIG. 4 depicts the plastic type classification for waste plastics recycling.

The preferred starting material for the present process is sorted waste plastics containing predominantly polyethylene and polypropylene (plastics recycle classification types 2, 4, and 5). The pre-sorted waste plastics are washed and shredded or pelleted to feed to a pyrolysis unit for thermal cracking. FIG. 4 depicts the plastic type classification for waste plastics recycling. Classification types 2, 4, and 5 are high density polyethylene, low density polyethylene and polypropylene, respectively. Any combination of the polyethylene and polypropylene waste plastics can be used. For the present process, at least some polyethylene waste plastic is preferred.

Proper sorting of waste plastics is very important in order to minimize contaminants such as N, Cl, and S. Plastics waste containing polyethylene terephthalate (plastics recycle classification type 1), polyvinyl chloride (plastics recycle classification type 3) and other polymers (plastics recycle classification type 7) need to be sorted out to less than 5%, preferably less than 1% and most preferably less than 0.1%. The present process can tolerate a moderate amount of polystyrene (plastics recycle classification type 6). Waste polystyrene needs to be sorted out to less than 30%, preferably less than 20% and most preferably less than 5%.

Washing of waste plastics removes metal contaminants such as sodium, calcium, magnesium, aluminum, and non-metal contaminants coming from other waste sources. Non-metal contaminants include contaminants coming from the Periodic Table Group IV, such as silica, contaminants from Group V, such as phosphorus and nitrogen compounds, contaminants from Group VI, such as sulfur compounds, and halide contaminants from Group VII, such as fluoride, chloride, and iodide. The residual metals, non-metal contaminants, and halides need to be removed to less than 50 ppm, preferentially less than 30 ppm and most preferentially to less than 5 ppm.

If the washing does not remove the metals, non-metal contaminants, and halide impurities adequately, then a separate guard bed can be used to remove the metals and non-metal contaminants.

The pyrolyzing is carried out by contacting a plastic material feedstock in a pyrolysis zone at pyrolysis conditions, where at least a portion of the feed(s) is cracked, thus forming a pyrolysis zone effluent comprising primarily olefins and paraffins. Pyrolysis conditions include a temperature of from about 400° C. to about 700° C., preferably from about 450° C. to about 650° C. Conventional pyrolysis technology teaches operating conditions of above-atmospheric pressures. See e.g., U.S. Pat. No. 4,642,401. Additionally, it has been discovered that by adjusting the pressure downward, the yield of a desired product can be controlled. See, e.g., U.S. Pat. No. 6,150,577. Accordingly, in some embodiments where such control is desired, the pyrolysis pressure is sub-atmospheric.

FIG. 2 shows one present integrated process where the entire pyrolysis oil (naphtha/diesel fraction and heavy fraction) is sent to a fluid catalytic cracking (FCC) unit 28.

The fluid catalytic cracking (FCC) process is widely used in the refining industry for conversion of atmospheric gas oil, vacuum gas oil, atmospheric residues and heavy stocks recovered from other refinery operations into high-octane gasoline, light fuel oil, heavy fuel oil, olefin-rich light gas (LPG) and coke. FCC uses a high activity zeolite catalyst to crack the heavy hydrocarbon molecules at a 950-990° F. reactor temperature in a riser with a short contact time of a few minutes or less. LPG streams containing olefins (propylene, butylene) are commonly upgraded to make alkylate gasoline, or to be used in chemicals manufacturing. A conventional FCC unit is used.

The refinery will generally have its own hydrocarbon feed flowing through the refinery units. The flow volume of pyrolysis oil and wax generated from the pyrolysis of waste plastic to the refinery units, here an FCC unit, can comprise any practical or accommodating volume % of the total flow to the refinery units. Generally, the flow of the pyrolysis oil and wax fraction generated from the waste plastic pyrolysis, for practical reasons, can be up to about 50 vol. % of the total flow, i.e., the refinery flow and the pyrolysis flow. In one embodiment, the flow of the pyrolysis oil is an amount up to about 20 vol. % of the total flow. In another embodiment, the flow of the pyrolysis oil and wax is an amount up to about 10 vol. % of the total flow. About 20 vol. % has been found to be an amount that is quite practical in its impact on the refinery while also providing excellent results and being an amount that can be accommodated. The amount of pyrolysis oil and wax generated from the pyrolysis can of course be controlled so that the fraction passed to the refinery units provides the desired volume % of the flow.

Cracking of the pyrolysis liquid oil and wax combined with petroleum derived oil in the FCC unit produces liquefied petroleum gas (LPG) olefin streams 31 and 32, as well as a gasoline 29 and heavy fraction 30. A $C_2^-$ offgas 33 is also produced.

The LPG olefin stream 31 is a $C_3$ liquid petroleum gas (LPG) fraction containing propane and propylene. This $C_3$ stream is a good feed for a steam cracker. The $C_3$ stream 31 is fed to a steam cracker 34 distillation section to separate into propane and propylene. Then, propane is fed to the reactor of steam cracker 34, there $C_3$ stream is ultimately converted to pure ethylene which is then polymerized 40. The polyethylene can then be used to produce polyethylene products 41.

The FCC gasoline 29 can be sent to a gasoline blending pool. The heavy portion 30 recovered from the FCC unit 28 is sent to appropriate refinery units 38 for upgrading into clean gasoline and diesel 39. The $C_4$ stream 32 is either sent to a gasoline blending pool or further upgraded into clean gasoline.

FIG. 3 shows a present integrated process where the entire pyrolysis oil (naphtha/diesel fraction and heavy fraction) is sent to a fluid catalytic cracking (FCC) unit 28 and then to an alkylation unit 35.

Similar to FIG. 2, cracking of the pyrolysis liquid oil and wax combined with petroleum derived oil in the FCC unit produces liquefied petroleum gas (LPG) olefin streams 31 and 32, as well as a gasoline 29 and heavy fraction 30. A $C_2^-$ offgas 33 is also produced.

The LPG olefin stream 31 is a $C_3$ liquid petroleum gas (LPG) fraction containing propane and propylene. This $C_3$ stream is a good feed for a steam cracker. The $C_3$ stream 31 is fed to a steam cracker 34. In the steam cracker 34, the $C_3$ stream is converted to pure ethylene which is then polymerized 40. The polyethylene can then be used to produce polyethylene products 41.

The LPG olefin stream 32 is a $C_4$ liquid petroleum gas (LPG) fraction containing butanes and butenes. This fraction can be sent to a refinery alkylation unit 35.

An alkylation process combines light olefins (propylene, butylene, typically from FCC unit) with isobutane to produce highly branched paraffinic fuel, alkylate gasoline. Alkylate gasoline is clean-burning, high-octane, low-sulfur, low-RVP gasoline blending component that does not contain olefinic or aromatic compounds, thus is a very desirable gasoline blending component. Conventional alkylation processes use either sulfuric acid catalyst which operates at 30-60° F. reactor temperature or hydrofluoric acid catalyst that operates at 90-95° F. reactor temperature. A conventional alkylation process can be used.

In the present process, an alkylate fraction comprising n-butane 36 is recovered from the alkylation unit 35. This fraction is rich in linear paraffins and a very good naphtha feed for the steam cracker 34 to generate ethylene. This n-butane feed 36 is therefore passed to the steam cracker 34 to produce ethylene, which is then polymerized 40. The polyethylene can then be used to produce consumer products 41.

The FCC gasoline 29 can be sent to a gasoline blending pool. A portion of the alkylate (alkylate gasoline) recovered from the alkylation unit can be combined/blended with the FCC gasoline fraction. The heavy portion 30 recovered from the FCC unit 28 is sent to appropriate refinery units 38 for upgrading into clean gasoline and diesel 39.

The steam cracker and ethylene polymerization unit is preferably located near the refinery so that the feedstocks (propane, butane, naphtha, propane/propylene mix) can be transferred via pipeline. For a petrochemical plant located away from the refinery, the feedstock can be delivered via truck, barge, rail car, or pipeline.

The benefits of a circular economy and an effective and efficient recycling campaign are realized by the present integrated process.

The following examples are provided to further illustrate the present process and its benefits. The examples are meant to be illustrative and not limiting.

Example 1: Properties of Pyrolysis Oil and Wax from Commercial Sources

Pyrolysis oil and wax samples were obtained from commercial sources and their properties are summarized in Table 1. These pyrolysis samples were prepared from waste plastics containing mostly polyethylene and polypropylene via thermal decomposition in a pyrolysis reactor at around 400-600° C., near atmospheric pressure without any added gas or a catalyst. A pyrolysis unit typically produces gas, liquid oil product, optionally wax product, and char. The pyrolysis unit's overhead gas stream containing thermally cracked hydrocarbon was cooled to collect condensate as pyrolysis oil (liquid at ambient temperature) and/or pyrolysis wax (solid at ambient temperature). The pyrolysis oil is the main product of the pyrolysis units. Some units produce pyrolysis wax as a separate product in addition to the pyrolysis oil.

TABLE 1

Properties of As-Received Oil and Wax from Pyrolysis of Waste Plastics

|  | Pyrolysis Oil Sample A | Pyrolysis Oil Sample B | Pyrolysis Oil Sample C | Pyrolysis Oil Sample D | Pyrolysis Wax Sample E |
|---|---|---|---|---|---|
| Specific Gravity at 60° F. | 0.814 | 0.820 | 0.774 | — | 0.828 |
| Simulated Distillation, ° F. | | | | | |
| 0.5% (Initial Boiling Point) | 87 | 299 | 18 | 86 | 325 |
| 5% | 179 | 306 | 129 | 154 | 475 |
| 10% | 214 | 309 | 156 | 210 | 545 |
| 30% | 322 | 346 | 285 | 304 | 656 |
| 50% | 421 | 447 | 392 | 421 | 733 |
| 70% | 545 | 585 | 517 | 532 | 798 |
| 90% | 696 | 798 | 663 | 676 | 894 |
| 95% | 772 | 883 | 735 | 743 | 939 |

TABLE 1-continued

Properties of As-Received Oil and Wax from Pyrolysis of Waste Plastics

|  | Pyrolysis Oil Sample A | Pyrolysis Oil Sample B | Pyrolysis Oil Sample C | Pyrolysis Oil Sample D | Pyrolysis Wax Sample E |
|---|---|---|---|---|---|
| 99.5% (Final Boiling Point) | 942 | 1079 | 951 | 888 | 1064 |
| Carlo-Erba Hydrocarbon Analysis | | | | | |
| Carbon, wt % | 87.6 | 84.21 | 85.46 | 85.97 | 85.94 |
| Hydrogen, wt % | 12.7 | 12.25 | 14.1 | 14.0 | 14.15 |
| Sum of C + H, wt % | 100.3 | 96.46 | 99.5 | 100.0 | 100.1 |
| H/C Molar Ratio | 1.73 | 1.75 | 1.98 | 1.96 | 1.98 |
| Bromine Number, g/ 100 g | 49 | 60 | 40 | 44 | 14 |
| Hydrocarbon Type | | | | | |
| Total Aromatics, vol % | 23.3 | 22.8 | 5.1 | 8.7 | 13.3 |
| Total Olefins & Naphthenes, vol % | 39.0 | 50.2 | 42.4 | 38.2 | 42.1 |
| Total Paraffins, vol % | 37.7 | 27 | 52.5 | 53.1 | 44.6 |
| Contaminants | | | | | |
| Total S, ppm | 48 | 29 | 7.8 | 99 | 6.3 |
| Total N, ppm | 751 | 1410 | 318 | 353 | 237 |
| Total Cl, ppm | 113 | 62 | 41 | 70 | 4.7 |
| O in naphtha & distillate, ppm | 250 | — | 574 | — | — |
| Trace Elemental Impurities | | | | | |
| Al, ppm | <1.1 | <0.56 | 0.6 | <0.53 | <0.68 |
| Ca, ppm | 1.4 | 11.5 | <0.5 | <0.53 | <0.68 |
| Fe, ppm | 4.9 | 11.9 | 1.6 | <1.1 | 3.1 |
| Mg, ppm | <0.51 | 1.3 | <0.52 | <0.53 | <0.68 |
| Na, ppm | 2.5 | <0.54 | <1.1 | <2.2 | <2.7 |
| Ni, ppm | <0.51 | <0.54 | <0.52 | 2 | <0.68 |
| V, ppm | <0.51 | <0.54 | <0.52 | 4 | <0.68 |
| P, ppm | 8.2 | 9.9 | <1.6 | <2.2 | 20.2 |
| Si, ppm | 82.5 | 49.6 | 13 | 17 | 3.1 |

ASTM D4052 method was used for specific gravity measurements. Simulated boiling point distribution curve was obtained using ASTM D2887 method. Carlo-Erba analysis for carbon and hydrogen was based on ASTM D5291 method. Bromine number measurement was based on ASTM D1159 method. Hydrocarbon-type analysis was done using a high resolution magnetic mass spectrometer using the magnet scanned from 40 to 500 Daltons. Total sulfur was determined using XRF per ASTM D2622 method. The nitrogen was determined using a modified ASTM D5762 method using chemiluminescence detection. The total chloride content was measured using combustion ion chromatography instrument using modified ASTM 7359 method. The oxygen content in naphtha and distillate boiling range was estimated using GC by GC/MS measurements with electron ionization detector for m/Z range of 29-500. Trace metal and non-metal elements in oil were determined using inductively coupled plasma-atomic emission spectrometry (ICP-AES).

Industrial pyrolysis process of sorted plastics, sourced predominantly from polyethylene and polypropylene waste, produced quality hydrocarbon streams with specific gravity ranging 0.7 to 0.9, and a boiling range from 18 to 1100° F. as in pyrolysis oil or pyrolysis wax.

The pyrolysis product is rather pure hydrocarbon made of mostly carbon and hydrogen. The hydrogen to carbon molar ratio varies from 1.7 to near 2.0. The Bromine Number is in the range of 14 through 60 indicating varying degrees of unsaturation coming from olefins and aromatics. The aromatic content is in the range of 5 to 23 volume % with a higher severity unit producing more aromatics. Depending on the process conditions of the pyrolysis unit, the pyrolysis products show paraffinic content ranging from mid-20 vol. % to mid-50 vol. %. The pyrolysis product contains a substantial amount of olefins. Samples A and B, pyrolysis oil produced under more severe conditions such as higher pyrolysis temperature and/or longer residence time, contain higher aromatic and lower paraffinic components, resulting H/C molar ratio of around 1.7 and high Bromine Number of 50-60. Samples C and D were produced at less severe conditions, and the pyrolysis oils are more paraffinic, resulting H/C molar ratio of close to 2.0 and Bromine Number around 40. Sample E, pyrolysis wax, is mostly paraffinic, saturated hydrocarbon with a substantial amount of normal hydrocarbons (as opposed to branched hydrocarbons) with low Bromine Number of only 14.

The following Examples 2 through 5 show the evaluation of waste plastics pyrolysis oil for transportation fuel.

Example 2: Fractionation of Pyrolysis Oil for Evaluation as Transportation Fuel

Sample D was distilled to produce hydrocarbon cuts representing gasoline (350° F.$^-$), jet (350-572° F.), diesel (572-700° F.) and the heavy (700° F.$^+$) fractions. Table 2 summarizes the boiling point distribution and impurity distributions among the distilled product fractions.

TABLE 2

Distillation of Pyrolysis Oil into Fuel Fractions

| Sample ID | Sample D | Sample F | Sample G | Sample H | Sample I |
|---|---|---|---|---|---|
| Intended Fraction | | Gasoline Cut | Jet Cut | Diesel Cut | Unconverted |
| Cut Point Target, °F. | | 350⁻ | 350-572 | 572-700 | 700⁺ |
| Distillation Actual Yields, wt % | | 37.2 | 38.0 | 15.0 | 9.3 |
| Simulated Distillation, F | | | | | |
| IBP (0.5 wt %) | 86 | 27 | 299 | 539 | 640 |
| 5 wt % | 154 | 98 | 345 | 557 | 684 |
| 10 wt % | 210 | 147 | 365 | 574 | 696 |
| 30 wt % | 304 | 222 | 416 | 597 | 727 |
| 50 wt % | 421 | 270 | 457 | 619 | 758 |
| 70 wt % | 532 | 291 | 492 | 644 | 808 |
| 90 wt % | 676 | 337 | 546 | 674 | 898 |
| 95 wt % | 743 | 347 | 554 | 683 | 953 |
| FBP (99.5 wt %) | 888 | 385 | 591 | 711 | 1140 |
| Total S, ppm | 99 | 52 | 35 | 80 | 320 |
| Total N, ppm | 353 | 215 | 556 | 232 | 467 |
| Total Cl, ppm | 70 | 181 | 27 | 12 | 13 |

Example 3: Evaluation of Pyrolysis Oil Cut for Gasoline Fuel

Sample F, a pyrolysis oil cut for gasoline fuel boiling range, was evaluated to assess its potential to use as gasoline fuel. Sample F has the carbon number range of C5-C12, typical of the gasoline fuel.

Due to the olefinic nature of the pyrolysis oil, oxidation stability (ASTM D525) and gum forming tendency (ASTM D381) were identified as the most critical properties to examine. Research octane number (RON) and motor octane number (MON) are also the critical properties for engine performance. The RON and MON values were estimated from detailed hydrocarbon GC analysis.

TABLE 3

Evaluation of Pyrolysis Oil Naphtha Fraction for Gasoline Fuel

| | Oxidation Stability, min | Washed Gum, mg/100 mL | RON | MON |
|---|---|---|---|---|
| Sample F | 90 | 5.0 | 71.4 | 67.7 |
| Reference gasoline | >1440 | 1 | 95.8 | 86.2 |
| 4/96 vol. % Blend of Sample F with reference gasoline | >1440 | 2.0 | 94.5 | 85.1 |
| 15/85 vol. % Blend of Sample F with reference gasoline | >1440 | 2.2 | 91.8 | 83.1 |

Sample F, a pyrolysis oil cut for gasoline fuel boiling range, cannot be used by itself as automotive gasoline fuel due to its poor quality. The gasoline fraction from the pyrolysis oil showed very poor oxidation stability in that Sample F failed only after 90 min compared to the target stability of longer than 1440 minutes. The pyrolysis gasoline exceeded the wash gum target of 4 mg/100 mL suggesting severe gum forming tendency. The pyrolysis gasoline has poor octane numbers compared to the reference gasoline. A premium unleaded gasoline was used as the reference gasoline.

We also examined the potential of blending of the pyrolysis gasoline cut for a limited amount to the reference gasoline. Our study showed that possibly up to 15 volume % of Sample F can be blended to the refinery gasoline while still meeting the fuels property targets. By integrating the pyrolysis gasoline product with a refinery fuel, the overall product quality can be maintained.

These results indicate that the as-produced gasoline fraction of pyrolysis oil has limited utility as gasoline fuel. Upgrading in a refinery unit is preferred to convert this gasoline fraction of the pyrolysis oil into hydrocarbon that meets the gasoline fuel property targets.

Example 4: Evaluation of Pyrolysis Oil Cut for Jet Fuel

Sample G, a pyrolysis oil cut for jet fuel boiling range, was evaluated to assess its potential to use as jet fuel. Sample G has the carbon number range of C9-C18, typical of the jet fuel.

Due to the olefinic nature of the pyrolysis oil, jet fuel thermal oxidation test (D3241) was considered as the most critical test. The pyrolysis oil jet cut as-is, Sample G, had only 36 minutes of oxidation stability suggesting the pure pyrolysis jet cut is unsuitable for use as jet fuel.

We prepared a 5 volume % blend of pyrolysis jet cut (Sample G) with refinery produced jet. The blend still failed for the jet fuel oxidation test as shown in Table 4.

TABLE 4

Evaluation of Pyrolysis Oil Jet Fraction for Jet Fuel

| | Jet Fuel Thermal Oxidation Test |
|---|---|
| Reference jet fuel | Passed |
| 5/95 vol. % Blend of Sample G with reference jet fuel | Failed |

These results indicate that the as-produced jet fraction of pyrolysis oil is completely unsuitable for jet fuel, and upgrading in a refinery unit is required to convert this jet fraction of the pyrolysis oil into hydrocarbon that meets the jet fuel property targets.

Example 5: Evaluation of Pyrolysis Oil Cut for Diesel Fuel

Sample H, a pyrolysis oil cut for diesel fuel boiling range, was evaluated to assess its potential to use as diesel fuel. Sample H has the carbon number range of C14-C24, typical of the diesel fuel.

Sample H contains a substantial amount of normal hydrocarbons. Since normal hydrocarbons tends to exhibit waxy characteristics, cold flow properties such as pour point (ASTM D5950-14) and cloud points (ASTM D5773) were considered as the most critical tests.

We prepared two blends at 10 and 20 volume % of Sample H with refinery produced diesel fuel. However, both blends still failed for the target pour point of less than −17.8° C. (0° F.) pour points.

TABLE 5

Evaluation of Pyrolysis Oil Diesel Fraction for Diesel Fuel

|  | Cloud Point (° C.) | Pour Point (° C.) | Pour Point Test |
|---|---|---|---|
| Reference diesel fuel | −17.1 | −19.0 | Passed |
| 10/90 vol. % Blend of Sample H with reference diesel fuel | −11.1 | −12.0 | Failed |
| 20/80 vol. % Blend of Sample H with reference diesel fuel | −5.5 | −7.0 | Failed |

These results indicate that the pyrolysis oil as-is is completely unsuitable for diesel fuel, and upgrading in a refinery unit is required to covert the diesel fraction of pyrolysis oil into hydrocarbon that meets the diesel fuel property targets.

Examples 6: Coprocessing of Pyrolysis Product to FCC Unit or FCC Pretreater Unit Results from Table 1 showed that industrial pyrolysis process of sorted plastics, sourced predominantly from polyethylene and polypropylene waste, produced quality pyrolysis oil or pyrolysis wax made of mostly carbon and hydrogen. With good sorting and efficient pyrolysis unit operation, the nitrogen and sulfur impurities are at low enough levels that a modem refinery can handle cofeeding of pyrolysis feedstocks to their processing units with no detrimental impacts.

However, some pyrolysis oils or wax may still contain high amounts of metals (Ca, Fe, Mg) and other non-metals (P, Si, Cl, O) that could negatively affect the performance of conversion units in a refinery. For pyrolysis products with high impurity levels are preferentially fed to a FCC feed treater unit before the FCC unit so that bulk of impurities are removed effectively by the pretreater.

By feeding the entire pyrolysis feedstock to a FCC unit as shown in FIG. 2 or to a FCC pretreater unit before the FCC unit, the pyrolysis oil and wax are converted into offgas, LPG paraffins and olefins, FCC gasoline and heavy hydrocarbon components. The FCC gasoline is a valuable gasoline blending component. The heavy fractions, light cycle oil (LCO) and heavy cycle oil (HCO) are converted further in the subsequent conversion units including jet hydrotreating unit, diesel hydrotreating unit, hydrocracking unit and/or coker unit to make more gasoline, jet, and diesel fuel with satisfactory product properties. The LPG paraffins and olefins are either processed further in an alkylation unit or in part used for petrochemicals production with a recycle content.

The following Examples 7 and 8 demonstrate the conversion of waste plastics pyrolysis product into quality transportation fuel in a refinery conversion unit, using a FCC unit as an example.

Example 7: Conversion of Pyrolysis Oil in FCC

To study the impact of coprocessing of waste plastics pyrolysis oil to FCC, series of laboratory tests were carried out with Samples A and C. Vacuum gas oil (VGO) is the typical feed for FCC. FCC performances of 20 volume % blend of pyrolysis oil with VGO and pure pyrolysis oil were compared with that of the pure VGO feed.

The FCC experiments were carried out on a Model C ACE (advanced cracking evaluation) unit fabricated by Kayser Technology Inc. using regenerated equilibrium catalyst (Ecat) from a refinery. The reactor was a fixed fluidized reactor using $N_2$ as fluidization gas. Catalytic cracking experiments were carried out at the atmospheric pressure and 900° F. reactor temperature. The cat/oil ratio was varied between 5 to 8 by varying the amount of the catalyst. A gas product was collected and analyzed using a refinery gas analyzer (RGA), equipped with GC with FID detector. In-situ regeneration of a spent catalyst was carried out in the presence of air at 1300° F., and the regeneration flue gas was passed through a LECO unit to determine the coke yield. A liquid product was weighted and analyzed in a GC for simulated distillation (D2887) and $C_5^-$ composition analysis. With a material balance, the yields of coke, dry gas components, LPG components, gasoline (C5-430° F.), light cycle oil (LCO, 430-650° F.) and heavy cycle oil (HCO, 650° F.$^+$) were determined. The results are summarized below in Table 6.

TABLE 6

Evaluation of Pyrolysis Oil Cofeeding to FCC

| Feed | 100% VGO | 20/80 vol % blend, Sample A/ VGO | 20/80 vol % blend, Sample C/ VGO | 100% Sample A | 100% Sample C |
|---|---|---|---|---|---|
| Cat/Oil, wt/wt | 6.0 | 6.0 | 6.0 | 6.0 | 6.0 |
| Conversion, wt %* | 81.3 | 83.15 | 83.09 | 76.1 | 78.82 |
| WLP Impurity** | | | | | |
| Total O, ppm | 81 | 76 | 62 | 54 | 67 |
| Total N, ppm | 27 | 30 | 33 | 50 | 21 |
| Yields | | | | | |
| Coke, wt % | 4.45 | 4.35 | 4.20 | 3.56 | 2.90 |
| Total Dry Gas, wt % | 2.08 | 1.96 | 1.93 | 1.55 | 1.43 |
| Hydrogen | 0.16 | 0.12 | 0.12 | 0.05 | 0.04 |
| Methane | 0.68 | 0.65 | 0.64 | 0.50 | 0.46 |
| Ethane | 0.44 | 0.43 | 0.41 | 0.33 | 0.28 |
| Ethylene | 0.76 | 0.74 | 0.72 | 0.63 | 0.61 |
| Total LPG, wt % | 21.25 | 21.08 | 21.50 | 20.17 | 24.40 |
| Propane | 1.78 | 1.76 | 1.72 | 1.47 | 1.53 |
| Propylene | 5.53 | 5.51 | 5.56 | 5.57 | 6.75 |
| n-Butane | 1.56 | 1.56 | 1.54 | 1.29 | 1.34 |

TABLE 6-continued

Evaluation of Pyrolysis Oil Cofeeding to FCC

| Feed | 100% VGO | 20/80 vol % blend, Sample A/ VGO | 20/80 vol % blend, Sample C/ VGO | 100% Sample A | 100% Sample C |
|---|---|---|---|---|---|
| Isobutane | 6.61 | 6.48 | 6.64 | 5.43 | 6.61 |
| C4 olefins | 5.77 | 5.77 | 6.04 | 6.41 | 8.16 |
| Gasoline, wt % | 53.53 | 55.75 | 55.46 | 62.53 | 61.75 |
| LCO, wt % | 12.89 | 12.23 | 11.93 | 10.37 | 8.03 |
| HCO, wt % | 5.81 | 4.63 | 4.98 | 1.82 | 1.50 |
| Octane Number*** | 88.05 | 84.57 | 82.79 | 73.75 | 75.41 |

*Conversion—conversion of 430° F.$^+$ fraction to 430° F$^-$
**Impurity level of N and O in whole liquid product in fuels boiling range by GC × GC, ppm
***Octane number, (R + M)/2, was estimated from detailed hydrocarbon GC of FCC gasoline.

The results in Table 6 show that up to 20 volume % cofeeding of pyrolysis oil only makes very slight changes in the FCC unit performance indicating coprocessing of pyrolysis oil up to 20% is readily feasible. The 20 volume % blending of Sample A or Sample C led to very slight reduction of coke and dry gas yields, slight increase in gasoline yield and slight decrease in LCO and HCO, which are favorable in most situations. With paraffinic nature of pyrolysis oil, the 20% blends of A and C lowered the Octane number by about 3-5 numbers. With refinery operational flexibility, these octane number debits can be compensated with blending or feeding location adjustments.

The FCC unit cracks the pyrolysis oil info fuel range hydrocarbons, reduces impurities, and isomerize n-paraffins to isoparaffins. All these chemistry will improve the fuel properties of the pyrolysis oil and wax. By cofeeding the pyrolysis oil through the FCC process unit with a zeolite catalyst, the oxygen and nitrogen impurities in the fuel range were reduced substantially, from about 300-1400 ppm N to about 30 ppm N and from about 250-540 ppm O to about 60-80 ppm O. The hydrocarbon composition of all these cofeeding products are well within the typical FCC gasoline range.

The FCC runs of 100% pyrolysis oil showed substantial debits of Octane numbers by about 13-14 numbers. This shows that coprocessing of pyrolysis oil is preferred over processing of pure 100% pyrolysis oil.

Example 8: Coprocessing of Pyrolysis Wax in FCC

To study the impact of coprocessing of waste plastics pyrolysis wax to FCC, series of laboratory tests were carried out with Sample E and VGO. FCC performances of 20% blend of pyrolysis wax with VGO and pure pyrolysis wax were compared with that of the pure VGO feed, similar to Example 7. The results are summarized below in Table 7.

TABLE 7

Evaluation of Pyrolysis Wax Cofeeding to FCC

| Feed | 100% VGO | 20/80 vol % blend, Sample E/ VGO | 100% Sample E |
|---|---|---|---|
| Cat/Oil, wt/wt | 6.5 | 6.5 | 6.5 |
| Conversion, wt %* | 82.75 | 84.17 | 91.31 |
| Yields | | | |
| Coke, wt % | 4.78 | 4.76 | 4.26 |
| Total Dry Gas, wt % | 2.11 | 2.05 | 1.79 |
| Hydrogen | 0.16 | 0.14 | 0.07 |
| Methane | 0.69 | 0.67 | 0.58 |
| Ethane | 0.44 | 0.43 | 0.37 |
| Ethylene | 0.78 | 0.77 | 0.73 |
| Total LPG, wt % | 21.71 | 23.15 | 31.79 |
| Propane | 1.87 | 1.93 | 2.28 |
| Propylene | 5.54 | 5.98 | 8.59 |
| n-Butane | 1.65 | 1.74 | 2.15 |
| Isobutane | 6.91 | 7.25 | 8.88 |
| C4 olefins | 5.74 | 6.25 | 9.89 |
| Gasoline, wt % | 54.16 | 54.21 | 53.47 |
| LCO, wt % | 12.42 | 11.59 | 6.71 |
| HCO, wt % | 4.83 | 4.24 | 1.99 |
| Octane Number** | 89.95 | 88.38 | 83.52 |

*Conversion—conversion of 430° F.$^+$ fraction to 430° F.$^-$
**Octane number, (R + M)/2, was estimated from detailed hydrocarbon GC of FCC gasoline.

The results in Table 7 shows that up to 20 volume % cofeeding of pyrolysis wax only makes very slight changes in the FCC unit performance indicating coprocessing of pyrolysis wax up to 20% is readily feasible. The 20 volume % blending of Sample E led to very slight reduction to no change of coke and dry gas yields, noticeable increase in LPG olefin yield, very slight increase in gasoline yield and slight decrease in LCO and HCO, which are all favorable in most situations. With paraffinic nature of pyrolysis wax, the 20% blend of Sample E lowered the Octane number slightly by 1.5 number. With refinery blending flexibility, this octane number debit can be easily compensated with minor blending adjustments.

The FCC run of 100% pyrolysis wax showed substantial increase in conversion, and debit of the Octane number by 6. This shows that coprocessing of pyrolysis wax is preferred over processing of 100% pyrolysis wax.

Example 9: Feeding of LPG Olefins from FCC Unit, which Coprocessed Waste Plastics Pyrolysis Product, to Refinery Alkylation Unit Cofeeding of pyrolysis oil and/or wax to a FCC unit, as shown in Examples 8 and 9, produces a substantial amount of $C_3$-$C_5$ olefins with a recycle content. The $C_4$ only stream containing recycled olefins is separated from FCC light-end recovery units, and then fed to an alkylation unit, as shown in FIG. 3. Reaction of LPG olefins and isobutane in the alkylation reactor produces propane, butane and alkylate gasoline with recycle contents. Alkylate gasoline and butane are valuable gasoline blending components. The clean butane and naphtha stream from the alkylation unit is a valuable feedstock for a steam cracker.

Example 10: Feeding of Recycled $C_3$ LPG Stream to Steam Cracker for Ethylene Production, Followed by Productions of Polyethylene Resin and Polyethylene Consumer Products Instead of sending all LPG olefin streams to the alkylation reactor, the $C_3$ LPG stream containing propane and propylene, produced via cofeeding of pyrolysis products to a FCC unit, is separated and fed to a steam cracker for production of ethylene with a recycle content, as shown in FIG. 2. Alternatively, only n-butane and/or naphtha stream from the alkylation plant could be fed to the steam cracker to produce ethylene. The ethylene is then processed to a polymerization unit to produce polyethylene resin containing some recycled-polyethylene/polypropylene derived materials while the quality of the newly produced polyethylene is indistinguishable to the virgin polyethylene made entirely from virgin petroleum resources. The polyethylene resin with the recycled material is then further processed to produce various polyethylene products to fit the needs of consumer products. These polyethylene consumer products now contains chemically recycled, circular polymer while qualities of the polyethylene consumer products are indistinguishable from those made entirely from virgin polyethylene polymer. These chemically recycled polymer products are different from the mechanically recycled polymer products whose qualities are inferior to the polymer products made from virgin polymers.

The foregoing examples together clearly show a new effective way to recycle a large quantity of polyethylene and polypropylene derived waste plastics via chemical recycling through pyrolysis followed by cofeeding of the pyrolysis products in a refinery via efficient integration. This integration allows quality fuels and circular polymer productions.

As used in this disclosure the word "comprises" or "comprising" is intended as an open-ended transition meaning the inclusion of the named elements, but not necessarily excluding other unnamed elements. The phrase "consists essentially of" or "consisting essentially of" is intended to mean the exclusion of other elements of any essential significance to the composition. The phrase "consisting of" or "consists of" is intended as a transition meaning the exclusion of all but the recited elements with the exception of only minor traces of impurities.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise that as specifically described without actually departing from the spirit and scope of the present invention as defined by the appended claims.

What is claimed is:

1. A continuous process for converting waste plastic into recycle for polyethylene polymerization comprising:
   (a) selecting waste plastics containing polyethylene and/or polypropylene;
   (b) passing the waste plastics from (a) through a pyrolysis reactor to thermally crack at least a portion of the polyolefin waste and produce a pyrolyzed effluent;
   (c) separating the pyrolyzed effluent into offgas, char and a pyrolysis oil and optionally pyrolysis wax comprising a naphtha/diesel fraction and a heavy fraction;
   (d) passing the pyrolysis oil and wax from (c) to a refinery FCC unit with the volume flow of pyrolysis oil and wax to the refinery FCC unit comprising up to but no more than 50 volume % of the total hydrocarbon flow to the FCC unit, with the remaining hydrocarbon flow to the refinery FCC unit comprising vacuum gas oil (VGO);
   (e) recovering a liquid petroleum $C_3$ olefin/paraffin mixture fraction from the FCC unit;
   (f) passing the liquid petroleum gas $C_3$ olefin/paraffin mixture fraction to a steam cracker for ethylene production; and
   (g) recovering a gasoline and heavy fraction from the refinery FCC unit, with the gasoline passed to a gasoline blending pool.

2. The process of claim 1, wherein a liquid petroleum $C_4$ olefin/paraffin mixture fraction comprising butanes and butenes is recovered from the FCC unit and passed to a refinery alkylation unit.

3. The process of claim 2, wherein an alkylate gasoline and n-butane fraction is recovered from the alkylation unit and passed to a stream cracker to generate ethylene.

4. The process of claim 2, wherein an alkylate gasoline fraction is recovered from the refinery alkylation unit.

5. The process of claim 1, wherein ethylene produced in (f) is subsequently polymerized.

6. The process of claim 5, wherein polyethylene products are prepared from the polymerized ethylene.

7. The process of claim 4, wherein gasoline recovered from the refinery FCC unit is combined with at least a portion of the alkylate gasoline fraction recovered from the alkylation unit.

8. The process of claim 2, wherein the amount of gasoline produced by the FCC and alkylation units is increased with recycled pyrolysis oil.

9. The process of claim 1, wherein at least some contaminants are removed from the recovered pyrolysis oil of step (c) before the oil is passed to the FCC unit in (d).

10. The process of claim 1, wherein the waste plastics selected in (a) are from plastics classification group 2, 4, and/or 5.

11. The process of claim 1, wherein the waste plastics passed from (a) contain less than 50 ppm halides.

12. The process of claim 1, wherein the waste plastics contain less than 5 wt. % polyethylene terephthalate and polyvinyl chloride.

13. A continuous process for converting waste plastic into recycle for polyethylene polymerization comprising:
   (a) selecting waste plastics containing polyethylene and/or polypropylene;
   (b) passing the waste plastics from (a) through a pyrolysis reactor to thermally crack at least a portion of the polyolefin waste and produce a pyrolyzed effluent;
   (c) separating the pyrolyzed effluent into offgas, char and a pyrolysis oil comprising a naphtha/diesel fraction and a heavy fraction;
   (d) passing the pyrolysis oil from to a refinery FCC unit with the volume flow of pyrolysis oil and wax to the refinery FCC unit comprising up to but no more than 50 volume % of the total hydrocarbon flow to the FCC unit, with the remaining hydrocarbon flow to the refinery FCC unit comprising vacuum gas oil (VGO);

(e) recovering a gasoline and heavy fraction from the refinery FCC unit;
(f) recovering a liquid petroleum gas $C_4$ olefin/paraffin mixture fraction comprising butanes and butenes from the FCC unit;
(g) passing the liquid petroleum gas $C_4$ olefin/paraffin mixture fraction to an alkylation unit;
(h) recovering n-butane and a portion of naphtha fraction from the alkylation unit; and
(i) passing the n-butane and a portion of naphtha fraction to a steam cracker for ethylene production.

14. The process of claim 13, wherein an alkylate gasoline fraction is recovered from the refinery alkylation unit.

15. The process of claim 13, wherein the gasoline recovered from the refinery FCC unit is combined with an alkylate gasoline fraction recovered from the alkylation unit.

16. The process of claim 13, wherein at least some contaminants are removed from the recovered pyrolysis oil of step (c) before the oil is passed to the FCC unit in (d).

17. The process of claim 13, wherein the waste plastics selected in (a) are from plastics classification group 2, 4, and/or 5.

18. The process of claim 15, wherein the amount of gasoline produced by the FCC and alkylation units is increased with recycled pyrolysis oil.

19. The process of claim 13, wherein ethylene produced in (i) is subsequently polymerized.

20. The process of claim 19, wherein polyethylene products are prepared from the polymerized ethylene.

21. The process of claim 13, further comprising collecting a $C_3$ olefin/paraffin mixture fraction from the FCC unit and passing the fraction to a steam cracker for ethylene production.

22. A continuous process for converting waste plastic into recycle for polyethylene polymerization comprising:
(a) selecting waste plastics containing polyethylene and/or polypropylene;
(b) passing the waste plastics from (a) through a pyrolysis reactor to thermally crack at least a portion of the polyolefin waste and produce a pyrolyzed effluent;
(c) separating the pyrolyzed effluent into offgas, char and a pyrolysis oil comprising a naphtha/diesel fraction and a heavy fraction;
(d) passing the pyrolysis oil from (c) to a refinery FCC unit with the volume flow of pyrolysis oil and wax to the refinery FCC unit comprising up to but no more than 50 volume % of the total hydrocarbon flow to the FCC unit, with the remaining hydrocarbon flow to the refinery FCC unit comprising vacuum gas oil (VGO);
(e) recovering a liquid petroleum gas $C_3$ olefin/paraffin mixture fraction from the FCC unit;
(f) separating the $C_3$ paraffin and $C_3$ olefin into different fractions;
(g) passing the $C_3$ paraffin fraction to a steam cracker for ethylene production; and
(h) recovering a gasoline and heavy fraction from the refinery FCC unit, with the gasoline passed to a gasoline blending pool.

* * * * *

UNITED STATES PATENT AND TRADEMARK OFFICE
CERTIFICATE OF CORRECTION

PATENT NO.  : 11,306,253 B2  
APPLICATION NO. : 17/131910  
DATED : April 19, 2022  
INVENTOR(S) : Timken et al.

Page 1 of 1

It is certified that error appears in the above-identified patent and that said Letters Patent is hereby corrected as shown below:

In the Claims

Claim 13, Column 18 Line 62, replace "passing the pyrolysis oil from to a refinery FCC unit" with --passing the pyrolysis oil to a refinery FCC unit--

Signed and Sealed this
Twenty-fifth Day of October, 2022

Katherine Kelly Vidal
*Director of the United States Patent and Trademark Office*